United States Patent
Minai et al.

(10) Patent No.: US 7,523,756 B2
(45) Date of Patent: Apr. 28, 2009

(54) SYSTEM FOR DETECTING POSITION OF CAPSULE ENDOSCOPE IN SUBJECT

(75) Inventors: Tetsuo Minai, Tokyo (JP); Hatsuo Shimizu, Tokyo (JP)

(73) Assignee: Olympus Corporation, Tokyo (JP)

( * ) Notice: Subject to any disclaimer, the term of this patent is extended or adjusted under 35 U.S.C. 154(b) by 168 days.

(21) Appl. No.: 11/018,693

(22) Filed: Dec. 21, 2004

(65) Prior Publication Data

US 2005/0139222 A1 Jun. 30, 2005

(30) Foreign Application Priority Data

Dec. 25, 2003 (JP) ............................. 2003-430405

(51) Int. Cl.
*A61B 19/00* (2006.01)
(52) U.S. Cl. .................................... 128/899
(58) Field of Classification Search ............... 600/9–15, 600/117, 409, 424; 128/899
See application file for complete search history.

(56) References Cited

U.S. PATENT DOCUMENTS

| 5,425,382 A * | 6/1995 | Golden et al. ............... 128/899 |
| 5,840,024 A * | 11/1998 | Taniguchi et al. ........... 600/424 |
| 6,263,230 B1 * | 7/2001 | Haynor et al. .............. 600/424 |
| 2003/0045790 A1 * | 3/2003 | Lewkowicz et al. ......... 600/407 |
| 2003/0085994 A1 * | 5/2003 | Fujita et al. .................... 348/77 |
| 2004/0111011 A1 * | 6/2004 | Uchiyama et al. ........... 600/160 |
| 2004/0143182 A1 * | 7/2004 | Kucera et al. ............... 600/424 |

FOREIGN PATENT DOCUMENTS

| JP | 55-103834 | 8/1980 |
| JP | 09-028662 | 2/1997 |
| JP | 9-503054 | 3/1997 |
| JP | 9-327447 | 12/1997 |
| JP | 2959723 | 7/1999 |
| JP | 2003-19111 | 1/2003 |
| JP | 2003-116781 | 4/2003 |
| JP | 2003-117004 | 4/2003 |

OTHER PUBLICATIONS

Abstract only of WO 95/08130 published Mar. 23, 1995.
Abstract only of JP 04-008341 published Jan. 13, 1992.
Full English language translation of Japanese Patent Application Publication No. 09-028662 published Feb. 4, 1997.
Full English language translation of Japanese Patent Application Publication No. 9-503054 published Mar. 25, 1997.
Full English translation of Japanese Patent No. 2959723 dated Jul. 30, 1999.

* cited by examiner

*Primary Examiner*—Charles A. Marmor, II
*Assistant Examiner*—Christine D Hopkins
(74) *Attorney, Agent, or Firm*—Scully, Scott, Murphy & Presser, P.C.

(57) ABSTRACT

A system is for detecting a position of a device. The device is swallowed, passes through a subject, and includes a magnetic field generator generating a constant magnetic field. The system also includes a position transducer. The position transducer includes a magnetic detector detecting an intensity of a magnetic field component parallel to a constant magnetic field output from the magnetic field generator, and a position processor calculating a position of the device in the subject based on the intensity detected by the magnetic detector.

5 Claims, 9 Drawing Sheets

SYSTEM FOR DETECTING POSITION OF CAPSULE ENDOSCOPE IN SUBJECT

CROSS-REFERENCE TO RELATED APPLICATIONS

This application claims priority to Japanese Patent Application No. 2003-430405 filed on Dec. 25, 2003, the disclosure of which is incorporated herein in its entirely.

BACKGROUND OF THE INVENTION

1) Field of the Invention

The present invention relates to a system for detecting a position of a device such as a capsule endoscope, which is swallowed and passes naturally through digestive tract of the subject, by a position transducer that is disposed on the outside of the subject and obtains information of the position of the device in the subject.

2) Description of the Related Art

In recent years, in the field of endoscopes, a swallowable capsule endoscope has been proposed. The capsule endoscope has an image capturing function and a radio communication function. The capsule endoscope has the function of traveling in the body cavity, for example, in the organs such as the stomach and the small intestine with peristalsis of the organs and sequentially capturing images for a period of time since the capsule endoscope is swallowed from the mouth of a subject for inspection (examination) until it is naturally excreted.

Image data captured in the body by the capsule endoscope as the capsule endoscope travels in the body cavity is sequentially transmitted by radio communication to the outside and stored into a memory provided on the outside. The subject can freely move throughout the period after he/she swallows the capsule endoscope until it is excreted by carrying a receiver having a radio communication function and a storing function. After the capsule endoscope is excreted, a doctor or nurse can display the images of the organs on a display based on the image data stored in the memory and make a check.

A capsule endoscope has been proposed in which the receiver has the function of detecting the position of the capsule endoscope in the subject to capture, for example, an endoscope image of a specific organ in the subject. As an example of a capsule endoscope system having the position detecting function, a capsule endoscope system using the radio communication function provided in the capsule endoscope is known. Specifically, the system has a configuration that a receiver provided on the outside of a subject has a plurality of antenna elements, and has the function of receiving a radio signal transmitted from the capsule endoscope by the plurality of antenna elements and, based on intensities received by the antenna elements, detecting the position of the capsule endoscope in the subject (see Japanese Patent Application Laid-open No. 2003-19111, for example).

SUMMARY OF THE INVENTION

It is an object of the present invention to at least solve the problems in the conventional technology.

A system according to one aspect of the present invention includes a device that is swallowed, passes through a subject, and includes a magnetic field generator generating a constant magnetic field; and a position transducer that includes a magnetic detector detecting an intensity of a magnetic field component parallel to a constant magnetic field output from the magnetic field generator, and a position processor calculating a position of the device in the subject based on the intensity detected by the magnetic detector.

The other objects, features, and advantages of the present invention are specifically set forth in or will become apparent from the following detailed description of the invention when read in conjunction with the accompanying drawings.

DETAILED DESCRIPTION

Exemplary embodiments of a system for detecting a position of a capsule endoscope in a subject relating to the present invention will be explained in detail below with reference to the accompanying drawings. It should be noted that the drawings are schematic ones and the relation between thickness and width of each part, the thickness ratio of the parts, and the like are different from real ones. Obviously, the drawings include parts having different relations of dimensions and ratios.

Figure 1:
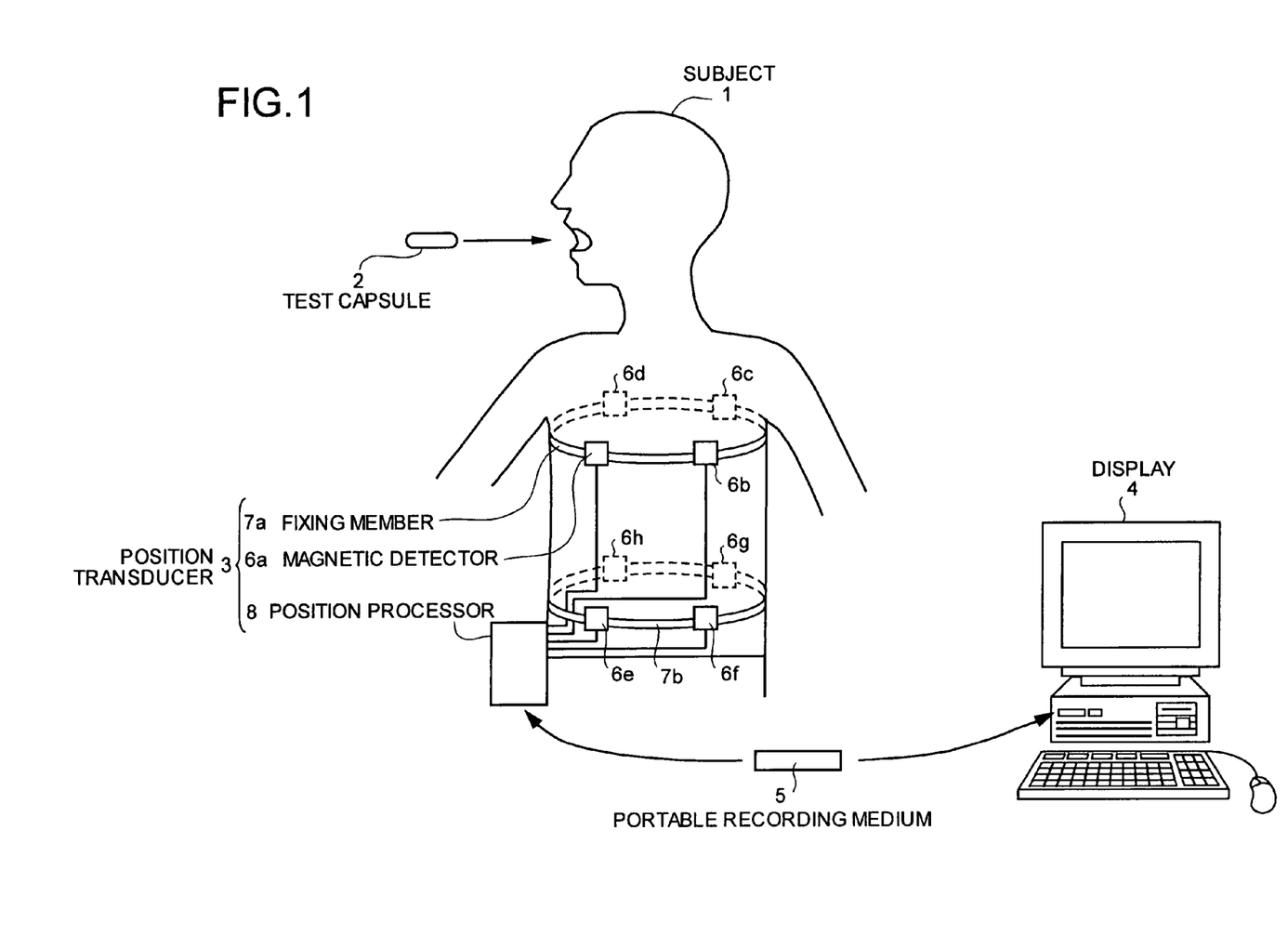
FIG. 1 is a schematic view of a system for detecting a position of a capsule endoscope in a subject according to a first embodiment.

A system for detecting a position of a capsule endoscope in a subject according to a first embodiment will now be explained. As shown in FIG. 1, the system for detecting a position of a capsule endoscope includes a test capsule 2 that is swallowed and passes though a subject 1 and functions as an example of a device to be traveled in a subject; a position transducer 3 that detects the position in the subject 1 of the test capsule 2; a display 4 displaying position information of the test capsule 2 detected by the position transducer 3; and a portable recording medium 5 for transmitting/receiving information between the position transducer 3 and the display 4.

The display 4 is used for displaying position information of the test capsule 2 obtained by the position transducer 3 and has a configuration like a workstation or the like that displays an image based on data obtained from the portable recording medium 5. Concretely, the display 4 may be constructed to directly display an image by a cathode-ray tube (CRT) display, a liquid crystal display, or the like or to output an image to another medium like a printer or the like.

The portable recording medium 5 can be inserted/removed to/from a position processor 8 that is explained later and the display 4, and has a structure capable of outputting and recording information when inserted to the position processor 8 and the display 4. Concretely, the portable recording medium 5 is inserted in the position processor 8 to record information on the position of the test capsule 2 while the test capsule 2 travels in the body cavity of the subject 1. After the test capsule 2 is excreted from the subject 1, the portable recording medium 5 is removed from the position processor 8 and inserted into the display 4, and the recorded data is read by the display 4. By transmitting data between the position processor 8 and the display 4 by the portable recording medium 5 such as a compact flash (trademark) memory, different from the case where the position processor 8 and the display 4 are connected to each other by wire, even when the test capsule 2 is traveling in the subject 1, the subject 1 can move freely.

The test capsule 2 is used at the time of conducting a preliminary inspection to check whether or not a narrow part in which passage of a capsule endoscope is difficult exists in the subject 1 before introduction of the capsule endoscope or the like into the subject 1. The system according to the first embodiment is used to check how the test capsule 2 travels in the subject 1. To achieve the purpose, a high-precision position detecting mechanism is provided.

Figure 2:
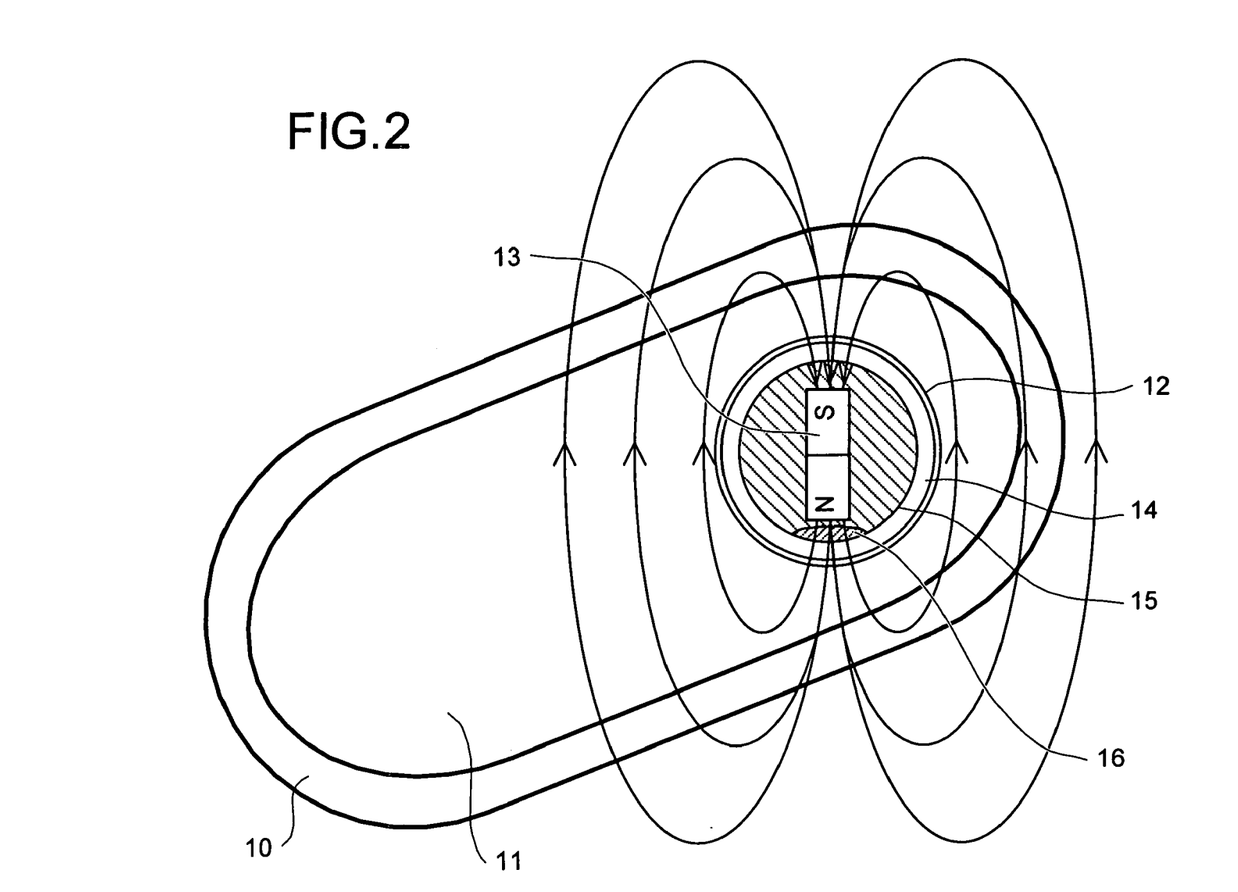
FIG. 2 is a schematic view of a test capsule as a component of the system according to the first embodiment.

FIG. 2 is a schematic diagram of the test capsule 2. As shown in FIG. 2, the test capsule 2 includes a casing 10 having a capsule shape that is similar to that of a casing of a capsule endoscope; a case member 12 held in the casing 10 and having a spherical shell shape; and a spherical body 15 disposed in a state where it floats in the liquid 14 held in the case member 12. The clearance between the inner surface of the casing 10 and the outer surface of the case member 12 is filled with a filling member 11.

The casing 10 is made of, for example, a bio-compatible material and has a characteristic such that when the casing 10 remains in the subject 1 for a few days, the material dissolves. By forming the casing 10 of a bio-compatible material, there is an advantage such that even if the test capsule 2 introduced in the subject 1 is not excreted to the outside of the subject 1, it is unnecessary to perform an abdominal operation or the like on the subject 1.

The filling member 11 is provided to fill the clearance between the inner face of the casing 10 and a permanent magnet 13 to fix the position of the permanent magnet 13. The material of the filling member 11 does not exert an adverse influence on the subject 1. For example, the filling member 11 is made of barium sulfate. Since barium sulfate can be used as a contrast medium in an X-ray inspection, position detection by an X-ray inspection can be performed in addition to the position detection of the first embodiment. By comparing the results of both of the inspections, more accurate position detection can be performed. Obviously, it is not essential to use barium sulfate as the filling member 11 in the first embodiment and an arbitrary material can be used as long as the material functions as the filling member.

The spherical body 15 has therein the permanent magnet 13 and a weighting member 16. The weighting member 16 is a member that is heavier than the other elements constructing the spherical body 15, and the spherical body 15 floats in the liquid 14 in a state where the weighting member 16 is positioned at the bottom in the vertical direction. As shown in FIG. 2, the weighting member 16 is disposed so as to position on extension line in the direction of an output magnetic field from the permanent magnet 13.

The permanent magnet 13 functions as a magnetic field generator in the claims, has a size that can be housed in the casing 10, and is to output a constant magnetic field whose intensity fluctuation with time is ignorable. As described above, the weighting member 16 is disposed on extension of the magnetic field output direction of the permanent magnet 13, so that the permanent magnet 13 maintains a state where the output magnetic field direction is parallel to the vertical direction irrespective of fluctuations in the orientation of the test capsule 2 by the action of the weighting member 16.

In place of the permanent magnet 13, for example, a coil that receives constant current and generates a constant magnetic field may be used as the magnetic field generator. In the case of using the permanent magnet 13, there is an advantage such that drive power is unnecessary. Thus, it is preferable to construct the magnetic field generator by using the permanent magnet 13.

The constant magnetic field generated from the permanent magnet 13 is expressed by a line of magnetic force of a closed curve that is output from the N pole side, travels on the outside of the permanent magnet 13, and enters again on the S pole side. As shown in FIG. 2, the travel direction of the line of magnetic force has location dependency but it can be regarded that the intensity of the constant magnetic field expressed by the line of magnetic force is determined only in accordance with the distance from the test capsule 2. Specifically, the size of the permanent magnet 13 provided in the test capsule 2 is small enough to be ignored as compared with the distance between the test capsule 2 and magnetic detectors 6a to 6h. Consequently, magnetic field intensity P at a point apart from the test capsule 2 only by distance "r" is expressed as follows by using a proportional factor α.

$$P=\alpha/r^3 \tag{1}$$

The system according to the first embodiment detects the position of the test capsule 2 based on the relation shown in Equation (1) as is explained later.

The position transducer 3 is explained. The position transducer 3 detects the position of the test capsule 2 in the subject 1 based on the constant magnetic field output from the test capsule 2. Concretely, the position transducer 3 has, as shown in FIG. 1, the magnetic detectors 6a to 6h for detecting the intensity of the constant magnetic field output from the test capsule 2, a fixing member 7a for fixing the magnetic detectors 6a to 6d to the subject 1, a fixing member 7b for fixing the magnetic detectors 6e to 6h to the subject 1, and the position processor 8 for calculating the position of the test capsule 2 based on the magnetic field intensities detected by the magnetic detectors 6a to 6h.

Figure 3:
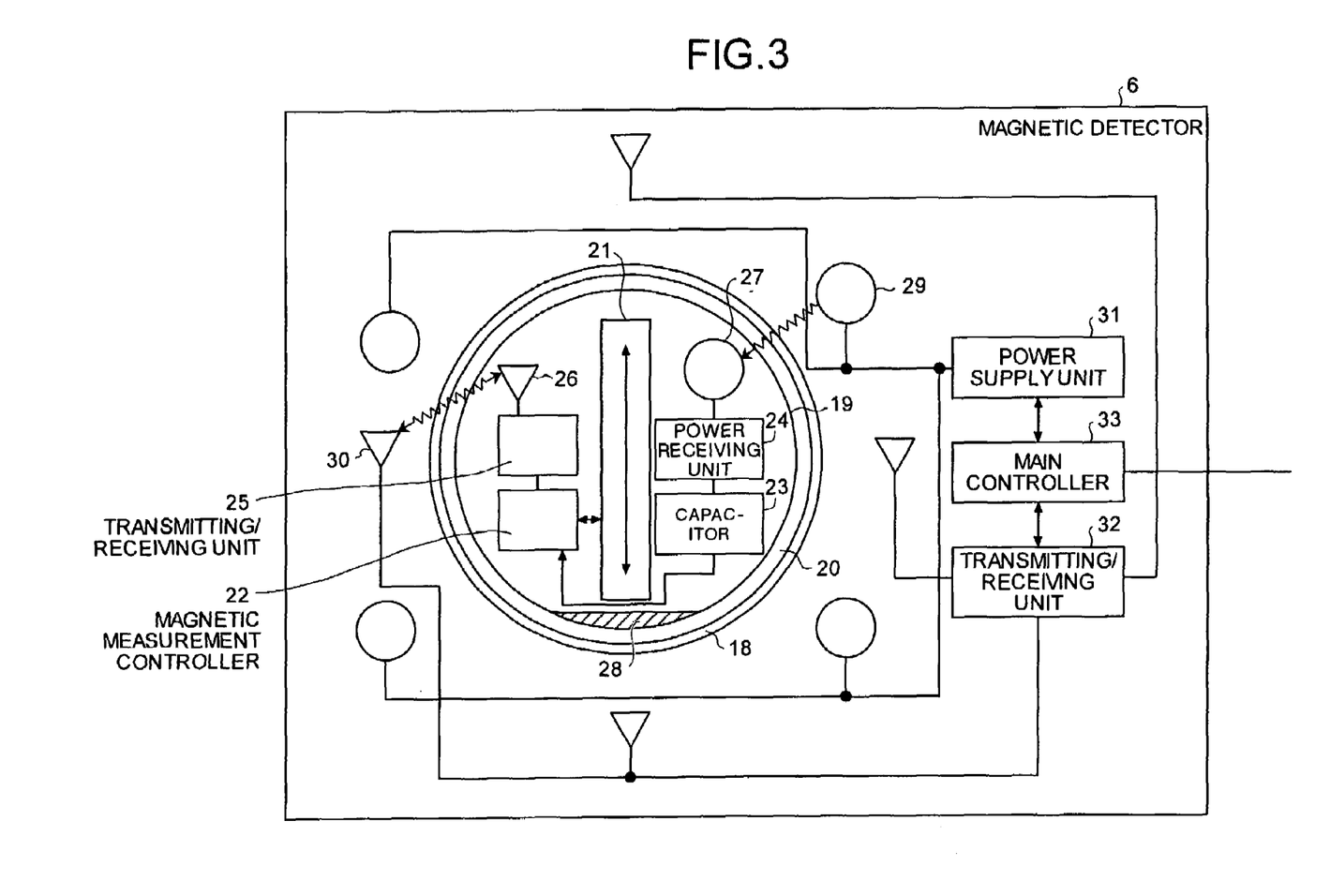
FIG. 3 is a schematic view of a magnetic detector as a component of the system according to the first embodiment.

Each of the magnetic detectors 6a to 6h is to detect the magnetic field intensity in the position where it is disposed. FIG. 3 is a schematic diagram of each of the magnetic detectors 6a to 6h. As shown in FIG. 3, each of the magnetic detectors 6a to 6h is constructed by a spherical body 19 having a magnetic sensor 21, a liquid 20 disposed so as to cover the outer surface of the spherical body 19 for holding the spherical body 19 in a floating state, a case member 18 for holding the liquid 20, and elements provided on the outside of the case member 18.

The spherical body 19 has a magnetic sensor 21, a magnetic measurement controller 22 that controls the driving state or the like of the magnetic sensor 21, a transmitting/receiving unit 25 that modulates/demodulates a signal as necessary at the time of performing radio communications with the outside of the spherical body 19, and a transmitting/receiving antenna 26 for performing radio communications with the outside. The spherical body 19 has a capacitor 23 that holds power to drive the magnetic sensor 21 and the like, a power receiving unit 24 that converts a power supply signal transmitted from the outside to power, and a power receiving antenna 27 for receiving the power supply signal transmitted from the outside and supplying it to the power receiving unit.

The spherical body 19 also has a weighting member 28 that is disposed on extension in the magnetic field detecting direction (that is explained later) of the magnetic sensor 21 and is made of a member heavier than the other elements. Since the spherical body 19 is held in a state where the spherical body 19 floats in the liquid 20, by the action of the weighting member 28, the spherical body 19 always maintains the state where the weighting member 28 is positioned at the bottom in the vertical direction irrespective of fluctuations in the state of the magnetic detector 6.

The magnetic sensor 21 takes the form of a magnetic field intensity sensor such as a magneto-impedance (MI) sensor having the function of detecting the magnetic field that travels in a predetermined direction (hereinbelow, the magnetic field direction will be called a "magnetic field detecting direction"). The MI sensor has a configuration using, for example, an FeCoSiB amorphous wire as a magneto-sensitive medium and senses the magnetic field intensity by using an MI effect that the magnetic impedance of the magneto-sensitive medium largely changes according to an external magnetic field when high-frequency current is passed to the magneto-sensitive medium. The magnetic sensor 21 has a magnetic field detecting direction shown by the arrow in FIG. 3 and has a configuration that the weighting member 28 is disposed on extension of the magnetic field detecting direction. Consequently, the magnetic sensor 21 is held in a state where the magnetic field detecting direction always coincides with the vertical direction, and senses the intensity of a magnetic field component traveling in the vertical direction among magnetic fields existing in the region where the magnetic detector 6 is disposed.

The magnetic detector 6 has, around the case member 18, a power supplying antenna 29 that transmits a power supply signal, a transmitting/receiving antenna 30 performing reception or the like of the magnetic field intensity detected by the magnetic sensor 21, a power supply unit 31 electrically connected to the power supplying antenna 29, and a transmitting/receiving unit 32 electrically connected to the transmitting/receiving antenna 30. The power supply unit 31 and the transmitting/receiving unit 32 are electrically connected to a main controller 33 and operate under control of the main controller 33. The main controller 33 is electrically connected to the position processor 8, operates under control of the position processor 8, and has the function of outputting the magnetic field sensed by the magnetic sensor 21 to the position processor 8.

The fixing members 7a and 7b fix the magnetic detectors 6a to 6h to the subject 1. Concretely, each of the fixing members 7a and 7b is formed, for example, of an elastic member in an annular shape and is fixed in a state where it is closely attached to the trunk of the subject 1. The magnetic detectors 6a to 6d and the magnetic detectors 6e to 6h are fixed to predetermined positions in the subject 1 by the fixing members 7a and 7b, respectively. By closely attaching the fixing members 7a and 7b to the trunk of the subject 1, the magnetic detectors 6a to 6h are disposed in a state where their relative positions to the subject 1 are fixed.

Figure 4:
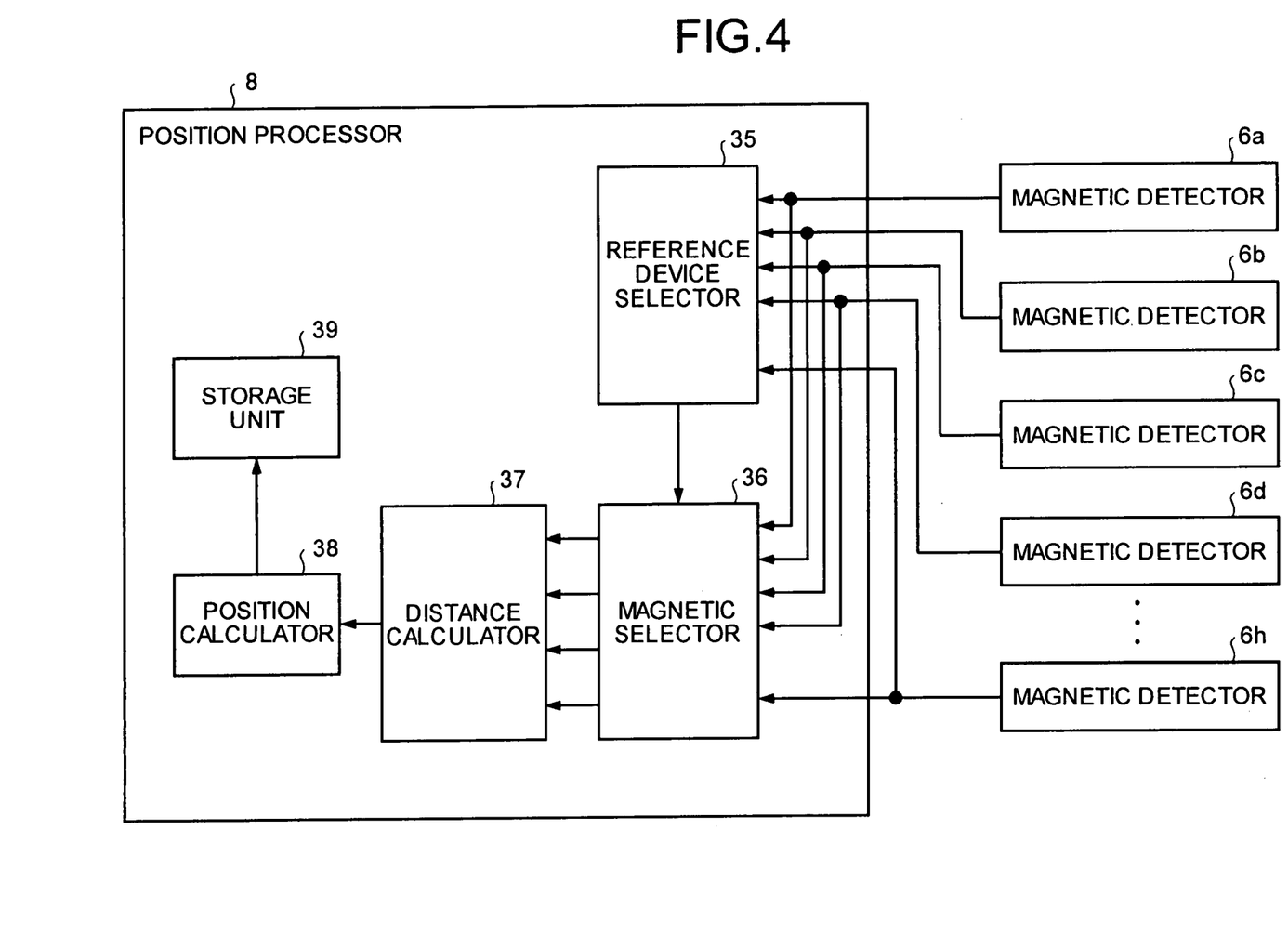
FIG. 4 is a schematic view of a position processor as a component of the system according to the first embodiment.

The position processor 8 calculates the position of the test capsule 2 based on the magnetic field intensities sensed by the magnetic detectors 6a to 6h. A concrete configuration of the position processor 8 is as shown in the block diagram of FIG. 4. As shown in FIG. 4, the position processor 8 includes a reference device selector 35 that selects a reference magnetic detector (hereinbelow, called "reference device") from the magnetic detectors 6a to 6h, and a magnetic selector 36 that outputs the magnetic field intensity obtained by the predetermined number of magnetic detectors based on the result of selection by the reference device selector 35. The position processor 8 includes a distance calculator 37 for calculating distance between the test capsule 2 and the reference device or the like based on the magnetic field intensity output from the magnetic selector 36; a position calculator 38 for calculating the position of the test capsule 2 by performing a computing process using the calculated distance and position coordinates of the reference device or the like used for calculating the distance; and a storage unit 39 for storing information of the position of the test capsule 2 obtained by the position calculator 38 into the portable recording medium 5.

The reference device selector 35 has the function of selecting the largest value of the detected magnetic field intensity from the magnetic detectors 6a to 6h. Concretely, the reference device selector 35 compares the magnetic field intensity values output from the magnetic detectors 6a to 6h with each other, selects the magnetic detector (reference device) that has output the largest magnetic field intensity value, and outputs information specifying the reference device (for example, information indicating the reference device among the magnetic detectors 6a to 6h) to the magnetic selector 36.

The magnetic selector 36 selects a plurality of magnetic detectors based on the result of selection of the reference device selector 35 and outputs the magnetic field intensities obtained by the selected magnetic detectors (selected devices) to the distance calculator 37. Concretely, the magnetic selector 36 has the function of selecting three magnetic detectors disposed in directions orthogonal to each other with respect to the reference device. Specifically, in the system according to the first embodiment, as also shown in FIG. 1, the magnetic detectors 6a to 6h are disposed so as to form vertexes of a cube, so that three magnetic detectors positioned in direction orthogonal to each other always exist for an arbitrary magnetic detector, and the magnetic selector 36 has the function of selecting the three magnetic detectors as selected devices.

The distance calculator 37 calculates the distances among the reference device, the selected devices, and the test capsule 2 based on the magnetic field intensities received via the magnetic selector 36. Concretely, the distance calculator 37 has the function of calculating the distance between the magnetic detector that has detected the magnetic field intensity and the test capsule 2 by performing the computing process shown by Equation (1) with respect to the input magnetic field intensity.

The position calculator 38 calculates the position of the test capsule 2 by performing a predetermined computing process based on the distance between the magnetic field intensity detecting device selected as a reference device or the like and the test capsule 2. The position calculator 38 also has the function of calculating the position of the test capsule 2 and, after that, outputting the result of calculation to the storage unit 39.

Figure 5:
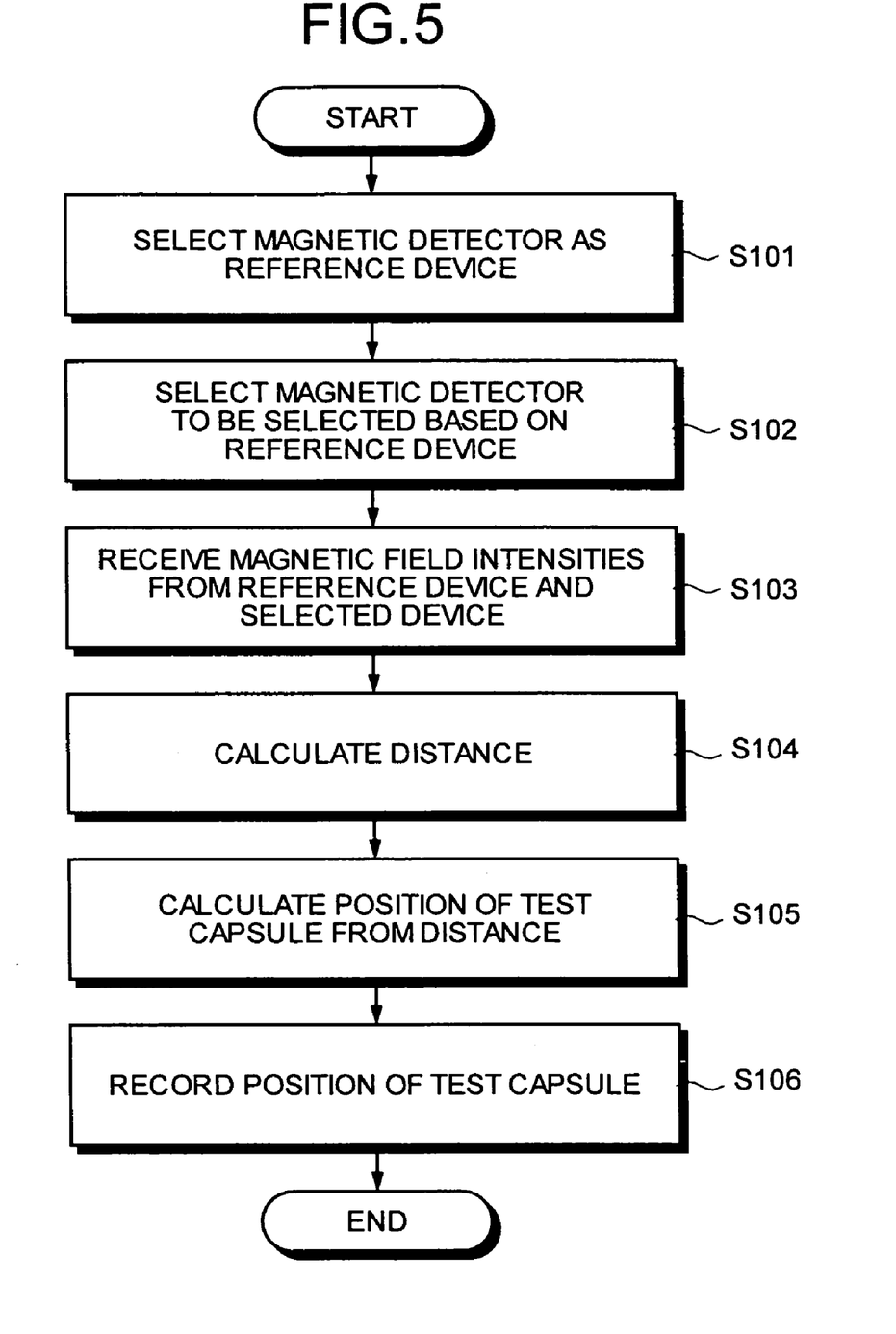
FIG. 5 is a flowchart of operations of the position processor.
Figure 6:
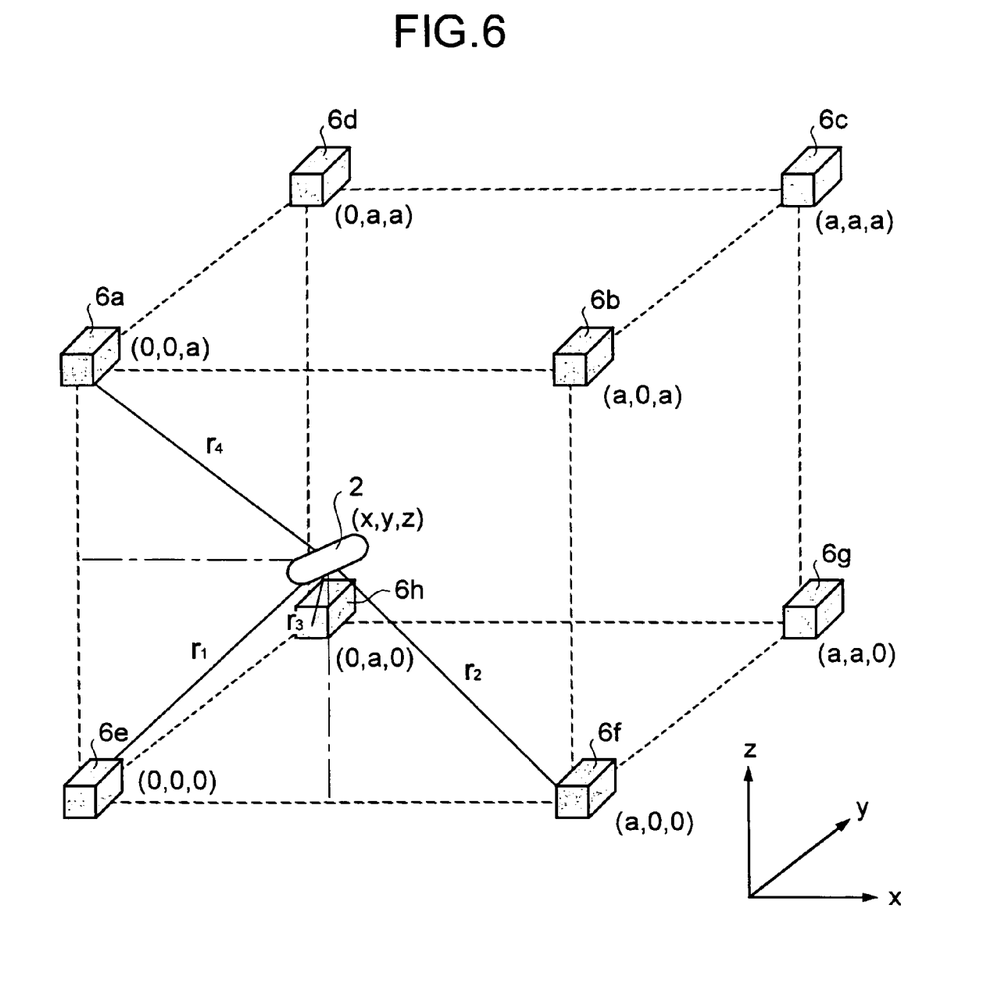
FIG. 6 is a schematic view of calculating the position of a test capsule by the position processor.

The operation of the position processor 8 in the first embodiment is explained. FIG. 5 is a flowchart that depicts the operation of the position processor 8, and FIG. 6 is a schematic diagram for explaining the algorithm of the position calculation. In FIG. 6, the length of one side of a cube constructed by the magnetic detectors 6a to 6h is set as "a". As is explained later, the position of the magnetic detector 6e selected as a reference device is set as the origin, the direction from the magnetic detector 6e toward the magnetic detector 6f is set as an x direction, the direction from the magnetic detector 6e toward the magnetic detector 6h is set as a y direction, and the direction from the magnetic detector 6e toward the magnetic detector 6a is set as a z direction. The positions of the magnetic detectors 6a to 6h are determined based on the xyz coordinate system, and the position of the test capsule 2 in the xyz coordinate system is expressed as (x,y,z). The operation of the position processor 8 is explained hereinbelow by properly referring to FIGS. 5 and 6.

First, the position processor 8 selects the magnetic detector having the magnetic field intensity that is the highest among the magnetic field intensities received by the magnetic detectors 6a to 6h (step S101). The example of FIG. 6 is a case where the magnetic detector 6e is selected as the magnetic detector sensing the highest magnetic field intensity. In the following description, it is also assumed that the magnetic detector 6e is the reference voltage.

The position processor 8 selects three devices by the magnetic selector 36 based on the reference device selected in step S101 (step S102), and outputs the magnetic field intensities obtained by the reference device and the selected devices to the distance calculator 37 (step S103). In the example of FIG. 6, the magnetic detectors 6f, 6h, and 6a are disposed in the directions orthogonal to each other with respect to the magnetic detector 6e as a reference device, so that the magnetic selector 36 selects the magnetic detectors 6f, 6h, and 6a as selected devices.

After that, the position processor 8 calculates the distance from the test capsule 2 based on the magnetic field intensity obtained by the reference device selected in step S101 and the magnetic field intensities obtained by the devices selected in step S102 by the distance calculator 37 (step S104). Concretely, the distance calculator 37 calculates the distance by performing computation of Equation (1) using the magnetic field intensity input via the magnetic selector 36. In the example of FIG. 6, the distance calculator 37 calculates distances $r_1$, $r_2$, $r_3$, and $r_4$ between the test capsule 2 and the magnetic detectors 6e, 6f, 6h, and 6a, respectively, based on the magnetic field intensities detected by the reference device and the selected devices.

The position processor 8 calculates the position of the test capsule 2 by the computing process in the position calculator 38 (step S105). Concretely, the position of the test capsule 2 is calculated by deriving the x coordinate, y coordinate, and z coordinate of the test capsule 2, so that the coordinates of the test capsule 2 are derived by using the coordinates of the magnetic detectors 6e, 6f, 6h, and 6a and the values of distances derived in step S104.

For example, the position coordinates (x,y,z) of the test capsule 2 can be geometrically derived from the positional relations shown in FIG. 6 and, concretely, can be calculated by solving the following equations.

$$(x-0)^2+(y-0)^2+(z-0)^2=r_1^2 \quad (2)$$

$$(x-a)^2+(y-0)^2+(z-0)^2=r_2^2 \quad (3)$$

$$(x-0)^2+(y-a)^2+(z-0)^2=r_3^2 \quad (4)$$

$$(x-0)^2+(y-0)^2+(z-a)^2=r_4^2 \quad (5)$$

In Equations (2) to (5), the number of unknown letters is three so that three equations are theoretically sufficient. At the time of actual position detection, however, to suppress deterioration in precision of the position detection of the test capsule 2 due to positional deviations of the magnetic detectors 6a to 6h, a distance derivation error, and the like, after solving Equations (2) to (5), the coordinates of the magnetic detector, and the like are corrected so that the values x, y, and z are unconditionally determined.

Finally, the position processor 8 stores the position of the test capsule 2 calculated in step S105 by the storage unit 39 (step S106). Concretely, while the test capsule 2 is swallowed in the subject 1, the portable recording medium 5 is inserted in the storage unit 39, so that the storage unit 39 records the position information obtained in step S105 into the portable recording medium 5.

The processes in steps S101 to S106 are repeatedly performed at predetermined time intervals. As a result, the portable recording medium 5 records information of travel in the subject 1 of the test capsule 2. After the test capsule 2 is excreted to the outside of the subject 1, the portable recording medium 5 is inserted to the display 4. The user grasps how the test capsule 2 travels in the subject 1 based on the result of recording displayed on the display 4 and determines the location of a narrow region existing in the subject 1 or the like from the grasped result.

The advantages of the system according to the first embodiment is explained. First, the system according to the first embodiment calculates the position of the test capsule 2 based on the constant magnetic field output from the permanent magnet 13 in the test capsule 2. Different from electromagnetic waves and the like, the constant magnetic field has a characteristic that its intensity attenuates almost unconditionally irrespective of physical parameters such as dielectric constant, magnetic permeability, and the like in a propagation region, so that the relation of Equation (1) is excellently satisfied. Therefore, the system has an advantage such that position detection can be performed with higher precision even in a space like the inside of a human body where organs and the like whose physical parameters are different from each other exist as compared with position detection using electromagnetic waves or the like.

Another advantage of using the constant magnetic field is that burden on the subject when the test capsule 2 is introduced into the subject 1 is lessened. For the above reasons, the system according to the first embodiment has an advantage such that deterioration in precision of the position detection due to variations of environments around the test capsule 2 is suppressed. Consequently, for example, at the time of introducing the test capsule 2 into the subject 1, it is unnecessary to impose limitations such as restriction on eating and drinking like in other inspecting methods. Therefore, the subject 1 can live normal life also at the time of an inspection using the test capsule 2 and the burden on the subject 1 in the inspection can be lessened.

In the system for detecting a position in a subject according to the first embodiment, the permanent magnet 13 held in the test capsule 2 maintains a state where the output magnetic field direction is parallel to the vertical direction irrespective of fluctuations in the orientation of the test capsule 2. The magnetic sensor 21 held in each of the magnetic detectors 6a to 6h maintains the state where the magnetic field detecting direction is parallel to the vertical direction irrespective of a change in the posture or the like of the subject 1. Thus, in the system for detecting a position in a subject according to the first embodiment, the state where the magnetic field output direction by the permanent magnet 13 and the magnetic field detecting direction of the magnetic sensor 21 are always parallel with each other is maintained.

By employing such a configuration, the system for detecting a position in a subject according to the first embodiment has an advantage such that the magnetic field intensity can be detected with high sensitivity. Specifically, most of the constant magnetic fields output from the permanent magnet 13 travel in the direction parallel to the magnetic field output direction also on the outside of the subject 1, and the magnetic field detecting direction of the magnetic sensor 21 becomes parallel to the magnetic field direction by the permanent magnet 13. Consequently, the constant magnetic field output from the permanent magnet 13 can be efficiently detected and high-sensitivity detection of the magnetic field intensity can be realized. To enjoy the advantage, it is sufficient that the magnetic field detecting direction of the magnetic sensor 21 and the magnetic field output direction by the permanent magnet 13 are parallel to each other. The directions do not always have to be parallel to the vertical direction.

Further, in the system for detecting a position in a subject according to the first embodiment, particularly, the configuration of the magnetic sensor with respect to the magnetic detectors 6a to 6h can be simplified. Specifically, when the magnetic field output direction from the permanent magnet 13 and the magnetic field detecting direction of the magnetic sensor do not have a correlation, the magnetic detector has to have magnetic field intensity detecting mechanisms in three axes directions. In such a case, generally, magnetic sensors having magnetic field detecting directions with respect to the x, y, and z directions have to be provided. In contrast, the system according to the first embodiment is disposed in a state where the magnetic field detecting direction of the magnetic sensor 21 coincides with the magnetic field output direction of the permanent magnet 13. Consequently, a magnetic field detecting mechanism having the function of detecting a magnetic field only in one direction can be employed and the configuration of the magnetic field detecting mechanism can be simplified.

The system according to the first embodiment has an advantage such that the influence of earth magnetic components can be eliminated. To be specific, the magnetic field output direction from the permanent magnet 13 is the vertical direction, and the magnetic detectors 6a to 6h have the function of detecting the intensity of magnetic field components in the vertical direction. On the other hand, the earth magnetic component travels in the direction almost perpendicular to the vertical direction, that is, almost in the horizontal direction. Consequently, the magnetic detectors 6a to 6h do not inherently detect the intensity of the earth magnetic component. Without providing a special filtering mechanism, the influence of the earth magnetic component can be eliminated.

Figure 7:
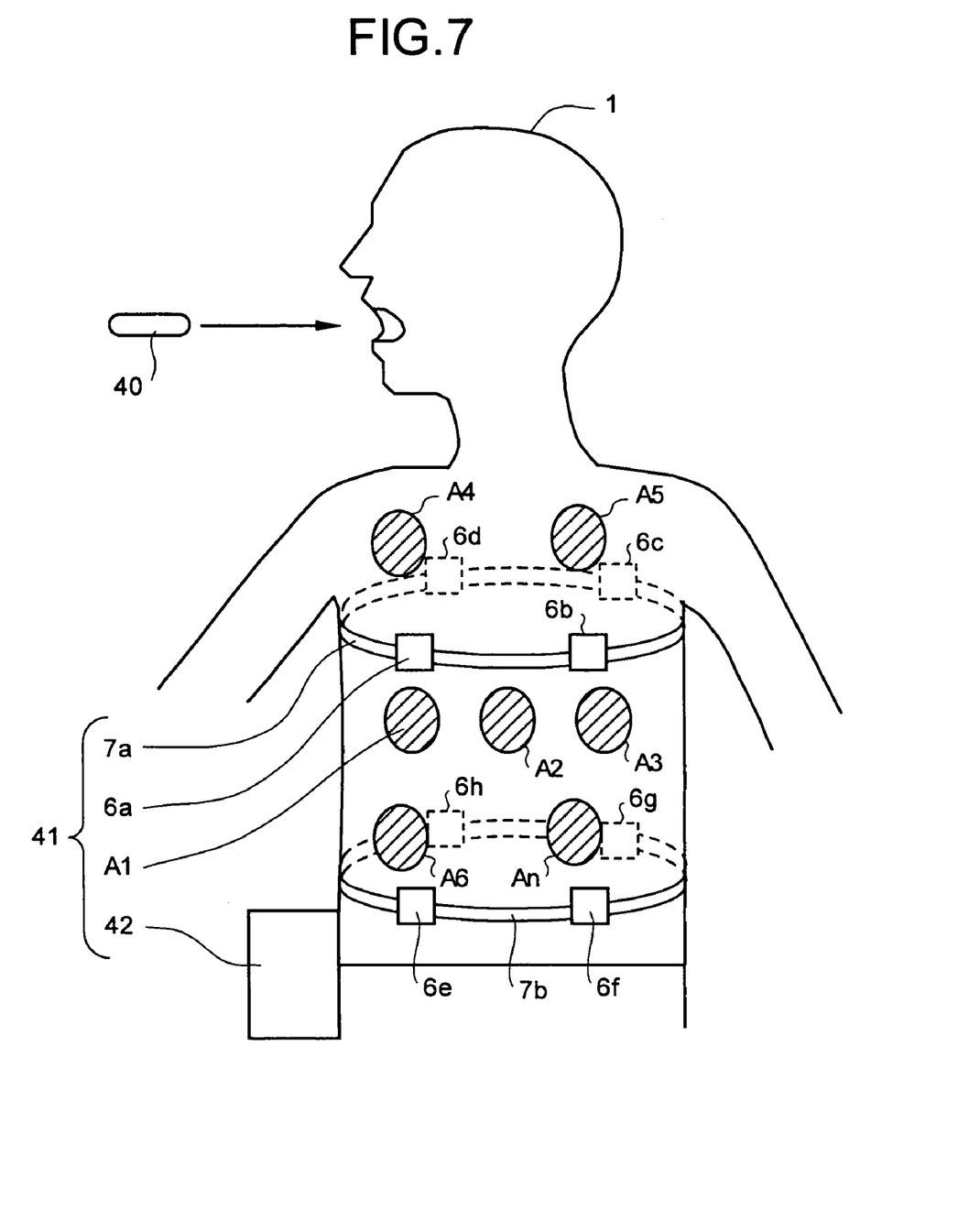
FIG. 7 is a schematic view of a system for detecting a position of a capsule endoscope in a subject according to a second embodiment.

A system for detecting a position of a capsule endoscope in a subject according to a second embodiment will now be explained. The system according to the second embodiment includes a capsule endoscope, as a device swallowed and passing through a subject, including not only the constant magnetic field generator but also a predetermined function executing unit and a radio unit; and a position processor for switching a plurality of antennas for receiving radio signals transmitted from the capsule endoscope based on the constant magnetic field generated by constant magnetic field generator and the result of detection of the position of the capsule endoscope in the subject.

FIG. 7 is a schematic diagram of the system according to the second embodiment. As shown in FIG. 7, the system according to the second embodiment includes a capsule endoscope 40 as an example of the device to be swallowed and passes through a subject, and a position transducer 41. Although elements corresponding to the display 4 and the portable recording medium 5 in the first embodiment are not shown in FIG. 7, it does not mean that those elements are excluded in the second embodiment. In the system according to the second embodiment, elements having the same reference numerals and names as those of the first embodiment have the same configurations and actions as those of the first embodiment unless otherwise specified in the following.

The position transducer 41 includes, as shown in FIG. 7, the magnetic detectors 6a to 6h, fixing members 7a and 7b for fixing the magnetic detectors 6a to 6h to the subject 1, receiving antennas $A_1$ to $A_n$ for receiving radio signals transmitted from the capsule endoscope 40, and a position processor 42 for processing the information obtained by the magnetic detectors 6a to 6h and the receiving antennas $A_1$ to $A_n$ and deriving information of the position in the subject 1, of the capsule endoscope 40. Although not shown in FIG. 7, the position transducer 41 has the function of supplying a power supply signal or the like to the capsule endoscope 40 as is explained later and has power supply antennas $B_1$ to $B_m$ for realizing the function.

The receiving antennas $A_1$ to $A_n$ are to receive radio signals transmitted from the capsule endoscope 40. As is explained later, the capsule endoscope 40 in the second embodiment has the function of capturing an image of the inside of the subject 1 and transmitting the image to the outside by radio. The receiving antennas $A_1$ to $A_n$ have the configuration of receiving a radio signal transmitted from the capsule endoscope 40 and outputting it to the position processor 42. The receiving antennas A1 to An are constructed by, concretely, for example, a loop antenna and a fixing unit that fixes the loop antenna to the subject 1. When radio signals are transmitted from the capsule endoscope 40, the radio signals may be received by all of the receiving antennas $A_1$ to $A_n$. However, in the second embodiment, the radio signal is received by using a receiving antenna that is determined to be most adapted to reception by an antenna selector 57 that is explained later among the plurality of receiving antennas $A_1$ to $A_n$.

Figure 8:
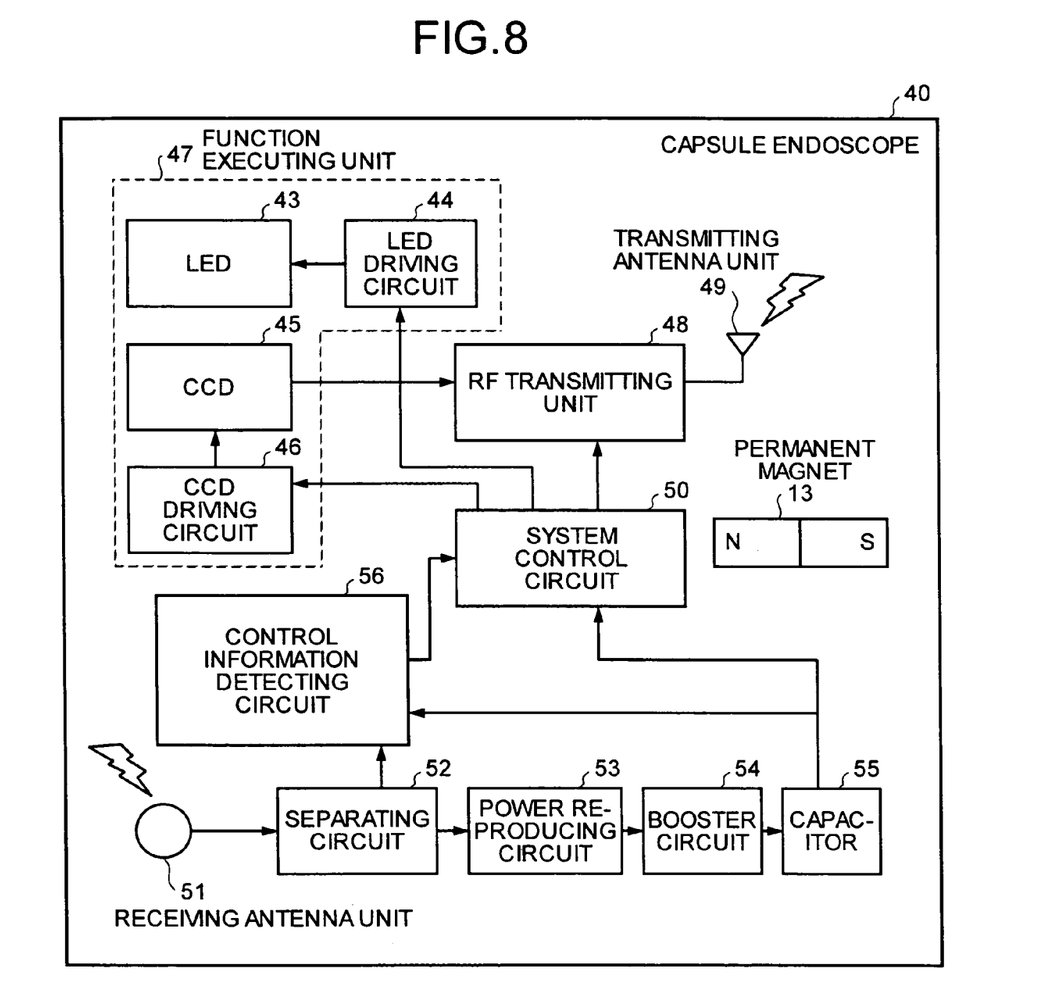
FIG. 8 is a schematic view of the capsule endoscope as a component of the system according to the second embodiment.

FIG. 8 is a block diagram of the capsule endoscope 40. The capsule endoscope 40 has, like the test capsule 2 in the first embodiment, the permanent magnet 13 as the magnetic field generator. Further, the capsule endoscope 40 includes a light emitting diode (LED) 43 functioning as a illuminating unit that illuminates an image capturing region at the time of capturing an image of the inside of the subject 1; an LED driving circuit 44 that controls a driving state of the LED 43; a charge-coupled device (CCD) 45 functioning as an image capturing unit for capturing a reflection light image from the region illuminated by the LED 43; and a CCD driving circuit 46 that controls a driving state of the CCD 45. The LED 43, LED driving circuit 44, CCD 45, and CCD driving circuit 46 are defined as a function executing unit 47 having a predetermined function as a whole.

The capsule endoscope 40 includes an RF transmitting unit 48 that modulates image data captured by the CCD 45, thereby generating an RF signal; a transmitting antenna unit 49 as a radio unit for transmitting the RF signal output from the RF transmitting unit 48 by radio; and a system control circuit 50 for controlling the operation of the LED driving circuit 44, CCD driving circuit 46, and RF transmitting unit 48.

By having the mechanisms, the capsule endoscope 40 obtains image data of a region to be tested that is illuminated by the LED 43 by the CCD 45 while the capsule endoscope 40 is introduced in the subject 1. The captured image data is converted to an RF signal by the RF transmitting unit 48 and, after that, the RF signal is transmitted to the outside via the transmitting antenna unit 49.

The capsule endoscope 40 also includes a receiving antenna unit 51 for receiving a radio signal sent from the position transducer 41 side; and a separating circuit 52 for separating the power supply signal from the signal received by the receiving antenna unit 51. The capsule endoscope 40 also includes a power reproducing circuit 53 for reproducing power from the separated power supply signal; a booster circuit 54 for boosting the reproduced power; and a capacitor 55 for storing the boosted power. The capsule endoscope 40 also includes a control information detecting circuit 56 for detecting a control information signal from the components separated from the power supply signal by the separating circuit 52 and outputting the detected control information signal to the system control circuit 50. The system control circuit 50 also includes the function of distributing drive power supplied from the capacitor 55 to the other elements.

By having the mechanisms, first, the capsule endoscope 40 receives the radio signal sent from the position transducer 41 side by the receiving antenna unit 51 and separates the power supply signal and the control information signal from the received radio signal by the separating circuit 52. The control information signal separated by the separating circuit 52 is output to the system control circuit 50 via the control information detecting circuit 56 and used for driving and controlling the LED 43, CCD 45, and RF transmitting unit 48. On the other hand, the power supply signal is reproduced as power by the power reproducing circuit 53. The potential of the reproduced power is boosted to potential adapted to the capacitor 55 by the booster circuit 54, and the boosted potential is stored in the capacitor 55.

Figure 9:
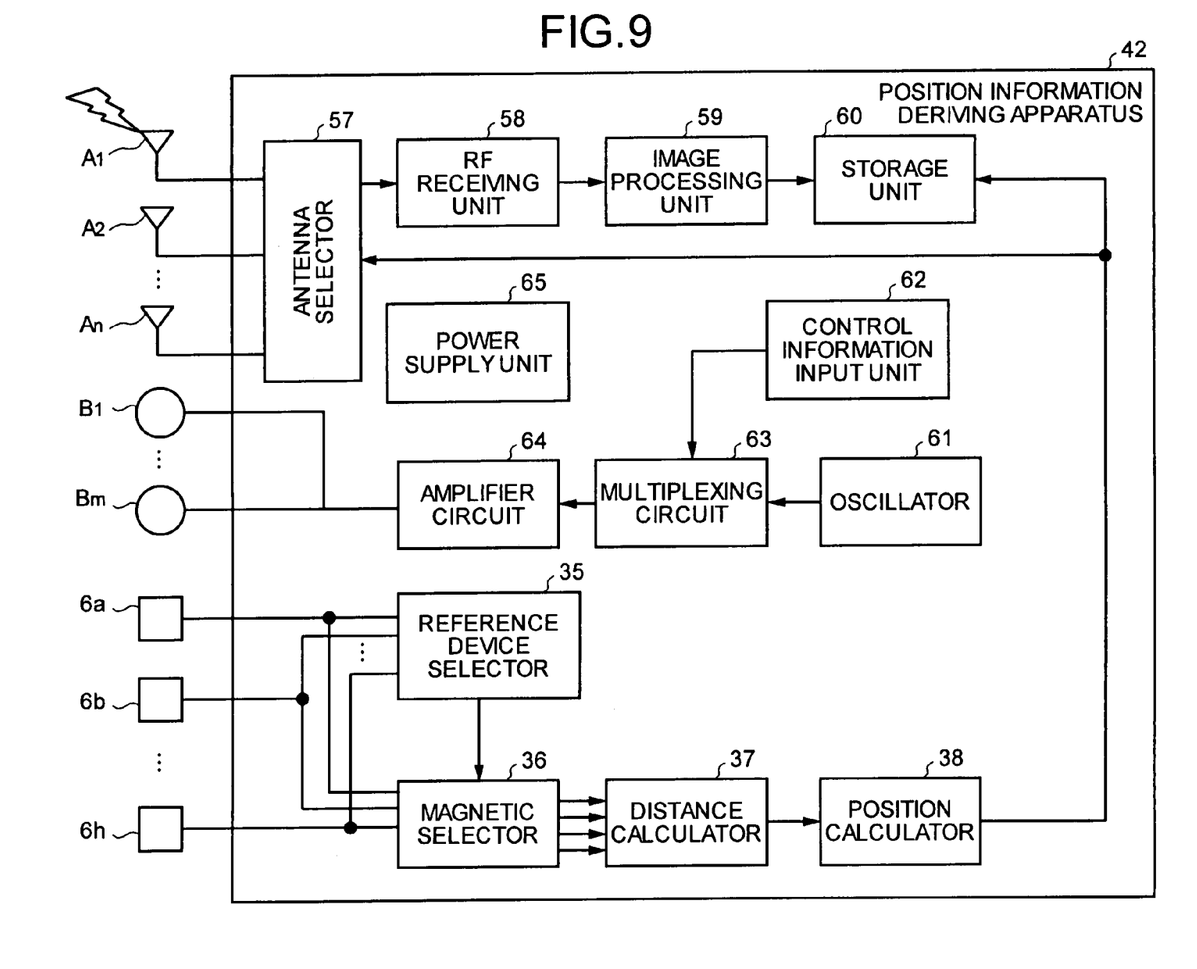
FIG. 9 is a schematic view of a position processor as a component of the system for detecting a position in a subject according to the second embodiment.

The configuration of the position processor 42 is explained. FIG. 9 is a block diagram of the position information driving apparatus 42. The position processor 42 in the second embodiment has, as elements for detecting the position in the subject 1 of the capsule endoscope 40, the reference device selector 35, magnetic selector 36, distance calculator 37, and position calculator 38. In the second embodiment, the magnetic detectors 6a to 6h output not only the magnetic field intensity but also the magnetic field direction to the position processor 42, so that the second embodiment is different from the first embodiment with respect to the following points. The reference device selector 35 extracts the magnetic field intensity from the information output from the magnetic detectors 6a to 6h to select a reference device, and the distance calculator 37 has the function of deriving distance by extracting the magnetic field intensities received by the reference device and the selected devices from the information input from the magnetic selector 36. The operation of detecting the position of the capsule endoscope 40 in the second embodiment is almost the same as that in the first embodiment and its detailed description will not be repeated.

The position processor 42 also includes the function of a receiving apparatus for receiving image data of the inside of the subject 1, which is sent from the capsule endoscope 40 by radio. Concretely, the position processor 42 has: the antenna selector 57 for selecting an antenna used for data reception from the receiving antennas $A_1$ to $A_n$; an RF receiving unit 58 that performs a predetermined process such as demodulation on a radio signal received by the selected receiving antenna, extracts image data captured by the capsule endoscope 40 from the radio signal, and outputs the extracted image data; an image processing unit 59 for performing a necessary process on the output image data; and a storage unit 60 for storing the processed image data.

The antenna selector 57 selects the receiving antenna that is most adapted to receive the radio signal transmitted from the capsule endoscope 40. Concretely, the antenna selector 57 grasps the positions of the receiving antennas A1 to An in advance and receives information of the position of the capsule endoscope 40 derived by the position calculator 38. The antenna selector 57 has the function of selecting a receiving antenna that is estimated to have the most excellent reception sensitivity based on the position of the capsule endoscope 40 and outputting a radio signal received by the selected receiving antenna to the RF receiving unit 58.

The storage unit 60 has the function of storing image data output from the image processing unit 59 and the position of the capsule endoscope 40 at the time point the output image data is captured in a state where the image data and the position of the capsule endoscope 40 are associated with each other. The position processor 42 has the configuration of outputting the information obtained by the position calculator 38 and the image processing unit 59 to the storage unit 60 as also shown in FIG. 9, and the storage unit 60 has the function of storing the information in the associated state. As a result, in the storage unit 60, the image data of a predetermined region in the subject 1 and the position of the capsule endoscope 40 at the time point the image data is captured is stored in a state where the image data and the position of the capsule endoscope 40 are associated with each other.

The position processor 42 also has the function of generating a power supply signal and the like transmitted to the capsule endoscope 40 and outputting the power supply signal to the power supply antennas $B_1$ to $B_m$. Concretely, the position processor 42 includes an oscillator 61 having the function of generating a power supply signal and the function of specifying an oscillation frequency; a control information input unit 62 that generates a control information signal for controlling the drive state of the capsule endoscope 40; a multiplexing circuit 63 for combining the power supply signal and the control information signal; and an amplifier circuit 64 for amplifying the intensity of the combined signal. The signal amplified by the amplifier circuit 64 is sent to the power supply antennas $B_1$ to $B_m$ and transmitted to the capsule endoscope 40. The position processor 42 includes a power supply unit 65 having a predetermined storage, an AC power adapter, or the like, and the elements of the position processor 42 uses the power supplied from the power supply unit 65 as driving energy.

The advantages of the system according to the second embodiment is explained. First, in the system according to the second embodiment, in a manner similar to the first embodiment, the capsule endoscope 40 includes therein the permanent magnet 13 and the position of the capsule endoscope 40 is detected based on the constant magnetic field output from the permanent magnet 13. As already mentioned above, the constant magnetic field has a characteristic that it attenuates almost unconditionally irrespective of the values such as dielectric constant, magnetic permeability, and the like in organs and the like in the subject 1. Consequently, there is an advantage such that the position of the capsule endoscope 40 can be accurately detected more than the case of performing position detection by using a radio signal.

The system for detecting a position in a subject according to the second embodiment has a configuration that the antenna selector 57 selects the receiving antenna based on the position of the derived capsule endoscope 40. The reception sensitivity of the radio signal in the receiving antenna depends on the distance from the capsule endoscope 40 and the orientation of the transmitting antenna unit 49 in the capsule endoscope 40. Therefore, a receiving antenna to be used can be accurately selected based on the capsule endoscope 40, and a position information detecting system capable of receiving a radio signal transmitted from the capsule endoscope 40 always at high sensitivity can be realized.

Further, the system according to the second embodiment has a configuration of outputting image data of the inside of the subject 1 captured and the derived position of the capsule endoscope 40 to the storage unit 60. Therefore, image data obtained by the capsule endoscope 40 and the derived position at the time of image capture of the capsule endoscope 40 can be stored so as to be associated with each other. At the time of displaying image data on the display 4, only the image data positioned in a predetermined range can be designated to be displayed. In other words, every image data is not displayed on the display 4 but image data of a region of interest of the user, for example, image data of only the small intestine can be displayed on the display 4. Thus, the position information detecting system that is convenient to doctors and the like can be realized.

Although the invention has been described above by the first and second embodiments, the invention is not limited to the foregoing embodiments and various embodiments, modifications, and application examples can be made by those skilled in the art. For example, in the first and second embodiments, the plurality of magnetic detectors 6 and the magnetic detector 6 are disposed on the outer surface of the subject 1 so as to detect the vertexes of a cube. However, the invention is not limited to the layout.

With respect to the magnetic detectors 6 and the like, it is sufficient to grasp relative positions to the subject 1 in advance. By using the relative positions, position detection is possible without disposing the magnetic detectors 6 in a cube shape. The number of the magnetic detectors 6 and the like is not limited to eight. As the simplest configuration, a system using a single magnetic detector 6 or the like can be constructed. Specifically, the test capsule 2 or the capsule endoscope 40 as the device to be introduced in the subject does not travel arbitrarily in the subject 1 but travels along a path that is determined to a certain degree of predetermined organs such as esophagus, stomach, small intestine, large intestine, and the like. Therefore, it is possible to preliminarily grasp a travel path of the device to be introduced in a subject to a certain degree. The position of the device to be introduced in a subject can be detected by using the path information grasped in advance and the intensity of the constant magnetic field received by the single magnetic detector.

Further, in the first and second embodiments, the reference device and the selected devices are selected by using the reference device selector 35 and the magnetic selector 36, and position detection is made based on the magnetic field intensities detected by the reference device and the selected devices. The configuration, however, is not essential to the invention. For example, it is also possible to derive the distance from the test capsule 2 or capsule endoscope 40 based on detected intensities with respect to all of the magnetic detectors 6a to 6h and generate eight ways of equations similar to Equations (2) to (5) to derive the position of the test capsule 2 or the like. In the case of the configuration, computation using, for example, the least square method is possible. Thus, there is an advantage such that an error of derivation of the position of the test capsule 2 or the like can be further reduced.

Although the function executing unit 47 having the CCD 45 and the like as an image capturing unit and the LED 43 and the like as an illuminating unit has been described in the second embodiment, the function executing unit 47 may obtain, in addition to the above, information of pH and the temperature in the subject 1. A configuration that the device to be introduced in a subject has an oscillator to capture an ultrasonic image of the inside of the subject 1 may be also employed. Further, a plurality of pieces of information may be obtained from the information of the inside of the subject.

The radio signal output from the power supply antennas $B_1$ to $B_m$ is not always limited to a signal obtained by multiplexing the control information signal and the power supply signal. Further, radio transmission from the position transducer to the capsule endoscope may not be performed. The power supply signal and a signal other than the control information signal may be multiplexed and the resultant signal may be transmitted. The position transducer 41 may receive only the radio signal output from the capsule endoscope. It is also possible to provide a storage unit in the capsule endoscope and, after the capsule endoscope is excreted to the outside of the subject, read information from the storage unit.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A system comprising:
  a device that is adapted to be swallowed and passed through a subject, and includes a magnetic field generator generating a constant magnetic field; and
  a position transducer that includes:
    a magnetic detector detecting an intensity of a magnetic field component in a vertical direction, the magnetic field component being a component of the constant magnetic field generated by the magnetic field generator; and
    a position processor calculating a position of the device in the subject based on the intensity detected by the magnetic detector;
  wherein the device further includes:
    a predetermined function executing unit that obtains information of an inside of the subject; and
    a radio transmitting unit that transmits the information of the inside of the subject with radio communication, and
    the position transducer further includes a receiving unit that receives a radio signal transmitted from the radio transmitting unit;
  wherein the position transducer includes a plurality of receiving units each receiving a radio signal transmitted from the radio transmitting unit, and a selector that selects a receiving unit used for receiving a radio signal based on the position calculated by the position processor.

2. The system according to claim 1, wherein the magnetic detector has a magnetic field detecting direction maintaining unit that maintains a magnetic field detecting direction in the vertical direction.

3. The system according to claim 1, wherein the magnetic field generator has a magnetic field output direction maintaining unit that maintains an output direction of the constant magnetic field in the vertical direction irrespective of fluctuations in an orientation of the device, and
  the magnetic detector has a magnetic field detecting direction maintaining unit that maintains the detecting direction of the magnetic field component in the vertical direction irrespective of fluctuations in a posture of the subject.

4. The system according to claim 1, wherein the position transducer includes a plurality of magnetic detectors, and
  the position processor calculates a distance between the device and each of the magnetic detectors based on intensities of magnetic field components detected by the magnetic detectors, and calculates a position of the device in a subject based on the calculated distances.

5. A system comprising:
  a device that is adapted to be swallowed and passed through a subject, and includes a magnetic field generator generating a constant magnetic field; and
  a position transducer that includes:
    a magnetic detector detecting an intensity of a magnetic field component in a vertical direction, the magnetic field component being a component of the constant magnetic field generated by the magnetic field generator; and a position processor calculating a position of the device in the subject based on the intensity detected by the magnetic detector;

wherein the device further includes:

a predetermined function executing unit that obtains information of an inside of the subject; and a radio transmitting unit that transmits the information of the inside of the subject with radio communication, and the position transducer further includes a receiving unit that receives a radio signal transmitted from the radio transmitting unit;

wherein the function executing unit includes:

an illuminating unit adapted to illuminate an inside of the subject; and an image capturing unit that captures an image of a region illuminated by the illuminating unit;

wherein the position transducer further includes a storage unit that stores an image captured by the image capturing unit and the position of the device at when the image is captured, so that the image and the position are associated with each other.

* * * * *